United States Patent [19]

Fujiki et al.

[11] Patent Number: 5,405,896
[45] Date of Patent: Apr. 11, 1995

[54] ADHESIVE SILICONE RUBBER COMPOSITIONS

[75] Inventors: Hironao Fujiki, Takasaki; Shigeki Shudo; Akira Matsuda, both of Annaka, all of Japan

[73] Assignee: Shin-Etsu Chemical Co., Ltd., Tokyo, Japan

[21] Appl. No.: 163,556

[22] Filed: Dec. 9, 1993

[30] Foreign Application Priority Data

Dec. 10, 1992 [JP] Japan .................. 4-352679

[51] Int. Cl.⁶ .................. C08K 5/24; C08F 8/00; C08L 83/00; C08G 77/06
[52] U.S. Cl. .................. 524/265; 524/268; 524/730; 524/731; 524/862; 525/100; 525/105; 525/106; 525/393; 525/431; 525/446; 525/464; 525/474; 528/15; 528/31; 528/32
[58] Field of Search .......... 524/730, 731, 265, 268, 524/862; 525/100, 105, 106, 393, 431, 446, 464, 474; 528/15, 31, 32

[56] References Cited

U.S. PATENT DOCUMENTS

| | | | |
|---|---|---|---|
| 4,584,355 | 4/1986 | Blizzard et al. | 525/477 |
| 4,585,836 | 4/1986 | Homan et al. | 525/477 |
| 4,591,622 | 5/1986 | Blizzard et al. | 525/477 |
| 4,774,297 | 9/1988 | Murakami et al. | 525/478 |
| 4,988,779 | 1/1991 | Medford et al. | 525/478 |
| 5,006,580 | 4/1991 | Kasuya et al. | 525/478 |

*Primary Examiner*—Melvyn I. Marquis
*Assistant Examiner*—Karen A. Dean
*Attorney, Agent, or Firm*—Birch, Stewart, Kolasch & Birch

[57] ABSTRACT

An adhesive silicone rubber composition of addition reaction curing type comprising (a) an organopolysiloxane containing an alkenyl group; (b) an organohydrogenpolysiloxane having at least one hydrogen atom directly attached to a silicon atom in a molecule; (c) an addition reaction catalyst; and (d) an adhesive agent selected from compounds of the following formulae (I), (II) and (III):

$$A-(D-B)_x-D-A \quad (I)$$

$$C-(B-D)_x-B-C \quad (II)$$

$$A-E \quad (III)$$

wherein each of A and B is a silane or siloxane group, each group having at least one hydrogen atom directly attached to a silicon atom and an optional substituent which is a substituted or unsubstituted monovalent hydrocarbon group having 1 to 8 carbon atoms attached to the same or different silicon atom, A being monovalent and B being divalent, each of C and D is a group having contained therein at least one member selected from the group consisting of a substituted or unsubstituted aryl group, a substituted or unsubstituted arylene group,

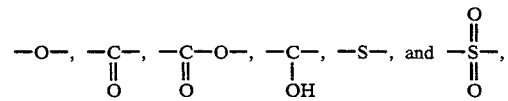

and an optional substituent which is selected from alkyl or alkylene groups, C being monovalent and D being divalent, E is a monovalent group as defined for C, with the proviso that the total number of atoms in E other than hydrogen and halogen atoms is at least 8, and letter x is 0 or a positive number, said adhesive silicone rubber composition giving a cured product that does not adhere to metal.

16 Claims, 1 Drawing Sheet

ADHESIVE SILICONE RUBBER COMPOSITIONS

BACKGROUND OF THE INVENTION

1. Field of the Invention

This invention relates to adhesive silicone rubber compositions which adhere well to organic resins, and more particularly, to silicone rubber compositions which adhere well to organic resins, but not to metals.

2. Prior Art

A number of methods have been proposed for providing a bond between addition curing type silicone rubber and organic resins. It is known, for example, to form a bond by applying a primer to a surface of molded resin, applying an uncured silicone rubber material thereto and curing the silicone rubber to the resin or by curing self-adhesive silicone rubber compositions directly to molded resin. For the self-adhesive silicone rubber compositions, a number of proposals have been made on their adhesive agent.

As another approach, it is known from Japanese Patent Publication (JP-B) No. 34311/1990 to add an organohydrogenpolysiloxane containing at least 30 mol % of hydrogen atoms directly attached to silicon atoms to an organic resin so that the resin is bondable with addition curing type silicone rubber. JP-B 45292/1988 discloses integration by physically fitting silicone rubber within a molded organic resin. In Japanese Patent Application Kokai (JP-A) No. 183843/1988, a compound having an aliphatic unsaturated group and a hydrolyzable group attached to a silicon atom is grafted to an olefin resin and silicone rubber is bonded and integrated with the grafted olefin resin. Furthermore, as we previously proposed, a thermoplastic resin can be bonded and integrated to a silicone rubber composition when a compound having an unsaturated group and a hydrogen atom directly attached to a silicon atom is added to the resin (U.S. Ser. No. 07/965,303, now U.S. Pat. No. 5,366,806 and EP 0540259 A1).

However, several problems arise with these prior art methods for integrating silicone rubber and organic resin into a one-piece article. The primer method is cumbersome in that a molded resin shape must be taken out of the mold before the primer can be applied thereto. The method of applying and curing a self-adhesive silicone rubber composition to molded resin has the serious problem that if the resin and silicone rubber are molded into a one-piece member using a mold, the silicone rubber itself adheres to the mold.

Little problem occurs when silicone rubber is coated and cured on resin preforms. However, for several of many general-purpose resins, for example, ABS, PPO, PPS, polycarbonate, acryl, PE, PP and Teflon, self-adhesive silicone rubber compositions of the addition curing type cannot provide a sufficient bond to allow utilization as one-piece articles.

When organohydrogenpolysiloxane is added to olefin resin, the properties of the resin itself can be altered thereby, preventing the resin from exerting its own properties. The physical engagement method leaves a possibility that the two segments will be disengaged by physical forces. When an olefin resin having grafted thereto a compound having an aliphatic unsaturated group and a hydrolyzable group attached to a silicon atom, a primer is required, when the olefin resin is to be joined to an addition curing type silicone rubber.

To take advantage of the weatherability, heat resistance, cleanliness and rubbery elasticity of silicone rubber, the demand that organic resin and silicone rubber be integrally molded into a one-piece article under curing conditions within a short time is increasing. There is a desire to have a silicone rubber composition capable of forming an effective bond to organic resins.

SUMMARY OF THE INVENTION

Therefore, an object of the present invention is to provide a novel and improved silicone rubber composition which can form a satisfactory bond to organic resins, especially thermoplastic resins under curing conditions within a short time and which itself, after curing, can be released from a metallic silicone rubber molding jig, typically a metallic mold, in a practically acceptable manner.

We have found that when a compound of formula (I), (II) or (III) defined below is blended in an adhesive silicone rubber composition of addition reaction curing type as an adhesive agent, the resulting silicone rubber composition can form a practically acceptable bond to organic resins, especially thermoplastic resins, but not to metals.

The adhesive silicone rubber composition of addition reaction curing type according to the present invention includes at least one member selected from compounds of the following general formulae (I), (II) and (III).

$$A-(D-B)_x-D-A \qquad (I)$$

$$C-(B-D)_x-B-C \qquad (II)$$

$$A-E \qquad (III)$$

Each of A and B is a silane or siloxane group, each group having at least one hydrogen atom directly attached to a silicon atom and an optional substituent which is a substituted or unsubstituted monovalent hydrocarbon group having 1 to 8 carbon atoms attached to a silicon atom, A being monovalent and B being divalent, each of C and D is a group having contained therein at least one member selected from the group consisting of a substituted or unsubstituted arylene group,

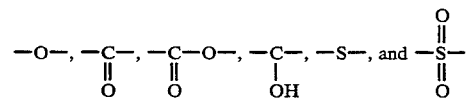

and an optional substituent which is selected from alkyl or alkylene groups, C being monovalent and D being divalent, E is a monovalent group as defined for C, with the proviso that the total number of atoms in E other than hydrogen and halogen atoms is at least 8, letter x is 0 or a positive number.

DETAILED DESCRIPTION OF THE INVENTION

Figure 1:
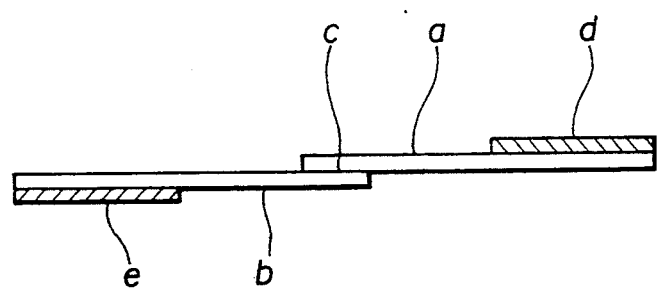
FIGS. 1A and 1B are side and plan views of an adhesion test piece.
Figure 1:
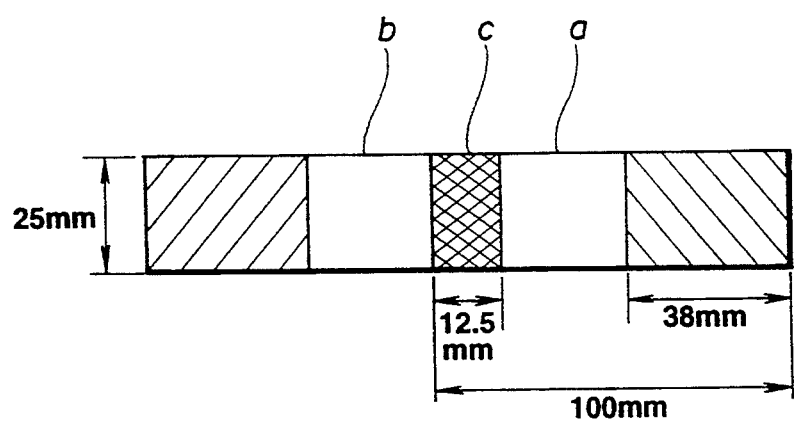

The present invention pertains to an adhesive silicone rubber composition of addition reaction curing type which includes at least one member selected from compounds of formulae (I), (II) and (III) as an adhesive agent.

The adhesive agent forms the essential part of the present invention. The minimum requirement for this component is that the compound contains at least one hydrogen atom directly attached to a silicon atom in a molecule and improves affinity to an organic resin to which the silicone rubber is to be joined. From the standpoint of joining silicone rubber to organic resin, it is preferred that the compound contains more than one hydrogen atom directly attached to a silicon atom in a molecule.

This, however, is not enough to establish a good adhesion to organic resins and it is additionally required that the adhesive agent be compatible with the organic resin to which silicone rubber is to be joined (to be referred to as adhered resin). From the standpoint of reactivity with the organic resin, the bond is significantly affected by a contact angle. The constituents contained in the adhesive agent depend on the adhered resin. Many adherend organic resins are generally composed of carbon, oxygen, nitrogen and sulfur atoms. To enhance affinity to such organic resins, the adhesive agent according to the invention should have a group as represented by C, D and E, in addition to a silane or siloxane group as represented by A and B.

More particularly, the adhesive agent is preferably in molten state under actual joining conditions and in that state, the compound should have a contact angle of up to 70° on the adhered organic resin (to which silicone rubber is to be joined) in order to effectively attain the objects of the invention. Measurement of the contact angle is generally at room temperature (25° C.), most preferably at the temperature during curing of the silicone rubber. If the adhesive agent component is solid or waxy at room temperature, it becomes necessary to measure the contact angle in molten state.

In order that those skilled in the art will more readily understand the concept of the adhesive agent according to the present invention, the concept intended herein is described below by way of illustration and not by way of limitation. We have found that (1) an effective factor contributing to adhesion to thermoplastic resins, that is, a major factor for the cohesive force developed between cured silicone rubber and thermoplastic resin is a hydrosilyl group ($\equiv$SiH). Although it is not certainly determined whether the hydrosilyl group undergoes hydrosilylation with the resin or undergoes hydrolysis to form a silanol ($\equiv$SiOH) which acts as a secondary cohesive force for the bond, the hydrosilyl group ($\equiv$SiH) greatly contributes to the bond. (2) Another important factor for adhesion is interaction with the thermoplastic resin. It is presumed that the fact that the adhesive agent includes a certain portion (a group as represented by C, D and E) having a molecular moiety compatible with the adhered resin, that is a thermoplastic resin will allow the adhesive agent to approach the thermoplastic resin close enough to generate a cohesive force therewith. This is the reason why the adhesive agent as defined herein is not included in the organohydrogenpolysiloxane which is conventionally used in addition reaction curing type silicone rubber compositions as a curing agent. More particularly, the organohydrogenpolysiloxane conventionally used as the curing agent is a compound having low surface tension, as is well known in the art, so that its contact angle with the resin surface is less than 70°, but it fails to exert adhesiveness as contemplated herein. This suggests that a group providing affinity to the organic resin is necessary in addition to the siloxane agent. More particularly, it is our understanding that in the structure of the adhesive according to the invention, the hydrosilyl group plays the role of a functional group exerting a cohesive force to the resin, and the groups of C, D and E other than the siloxane group plays the role of permitting the adhesive agent to approach toward the resin within a zone where a cohesive force to the resin is possible. To this end, the relevant portion should preferably have an analogous structure to the particular organic resin to which the silicone rubber is to be joined. The contact angle is one factor indicative of the analogous structure.

Where the adhesive agent contains a nitrogen atom, its molecule will be increased in polarity due to the nitrogen atom. In practice, such adhesive agent is not acceptable as the adhesive agent according to the invention because it is not only very effective in providing adhesion to resins, but also promotes adhesion to metals. Also simply for the purpose of providing adhesion to resins, many conventional well-known adhesive agent will be effective. Such typical adhesive agents are compounds having both a hydrogen atom directly attached to a silicon atom and at least one member of an alkoxysilyl, glycidyl and acid anhydride group in a molecule. These compounds are effective for adhesion to certain types of thermoplastic resins. It has been found that by introducing an unsaturated group into an adhered organic resin for modification or simple addition in mixed state, the bond between the (modified) resin and the silicone rubber (containing the tackifier component) is enhanced in a reliable manner. However, these adhesive agents have the drawback in that they also provide sufficient adhesion to metals as opposed to the subject matter of the present invention.

Therefore, in order to avoid adhesion to metallic molds, the adhesive agent used in the present invention should preferably be selected from the compounds which are free of adhesive functional groups as exemplified above, for example, trialkoxysilyl, glycidyl and acid anhydride groups. It is to be noted that compounds having such a functional group can be used without problem insofar as the functional group is fully suppressed in reactivity by the steric restraint or electronic action of a substituent group or neighbor group.

As understood from the above discussion, the adhesive agent should be selected from the compounds of formulae (I), (II) and (III) having a group of A or B having at least one, preferably at least two SiH groups and a group of C, D or E in a molecule.

Each of the linkages represented by C, D and E should preferably contain therein at least one group selected from the following formulae (1) to (10).

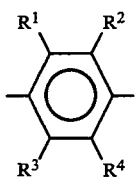
(1)

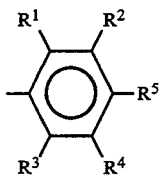
(2)

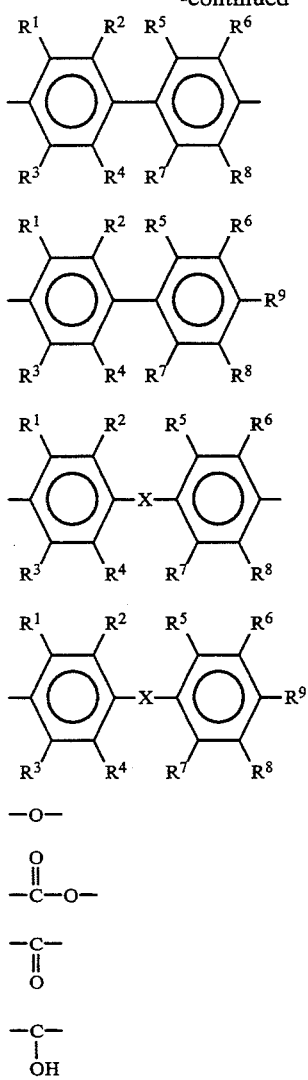

(3)
(4)
(5)
(6)
(7)
(8)
(9)
(10)

Each of $R^1$ to $R^9$, which may be identical or different, is a monovalent group selected from the group consisting of a hydrogen atom, halogen atom, hydroxyl group, substituted or unsubstituted monovalent hydrocarbon group having 1 to 8 carbon atoms, and alkoxy group having 1 to 6 carbon atoms;

X is a divalent group selected from the group consisting of

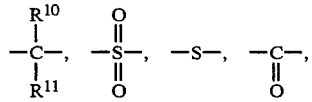

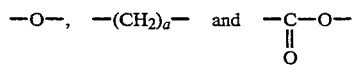

wherein each of $R^{10}$ and $R^{11}$, which may be identical or different, is a monovalent group selected from the group consisting of a hydrogen atom, halogen atom, and substituted or unsubstituted monovalent hydrocarbon group having 1 to 8 carbon atoms, or $R^{10}$ and $R^{11}$ taken together form a carbocyclic or heterocyclic ring, and letter a is an integer of at least 2.

Examples of the monovalent hydrocarbon group represented by $R^1$ to $R^{11}$ are the same as will be later described for R. Examples of the carbocyclic and heterocyclic rings formed by $R^{10}$ and $R^{11}$ taken together are given below.

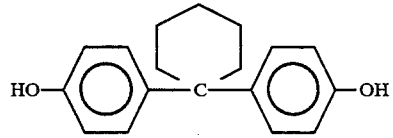

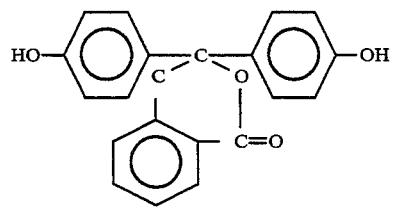

Exemplary compounds included in the tackifier component are given below.

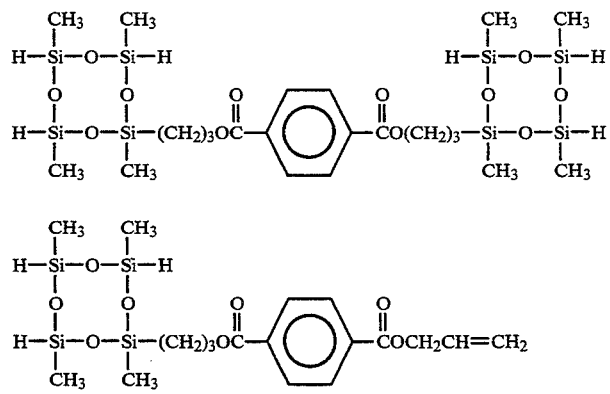

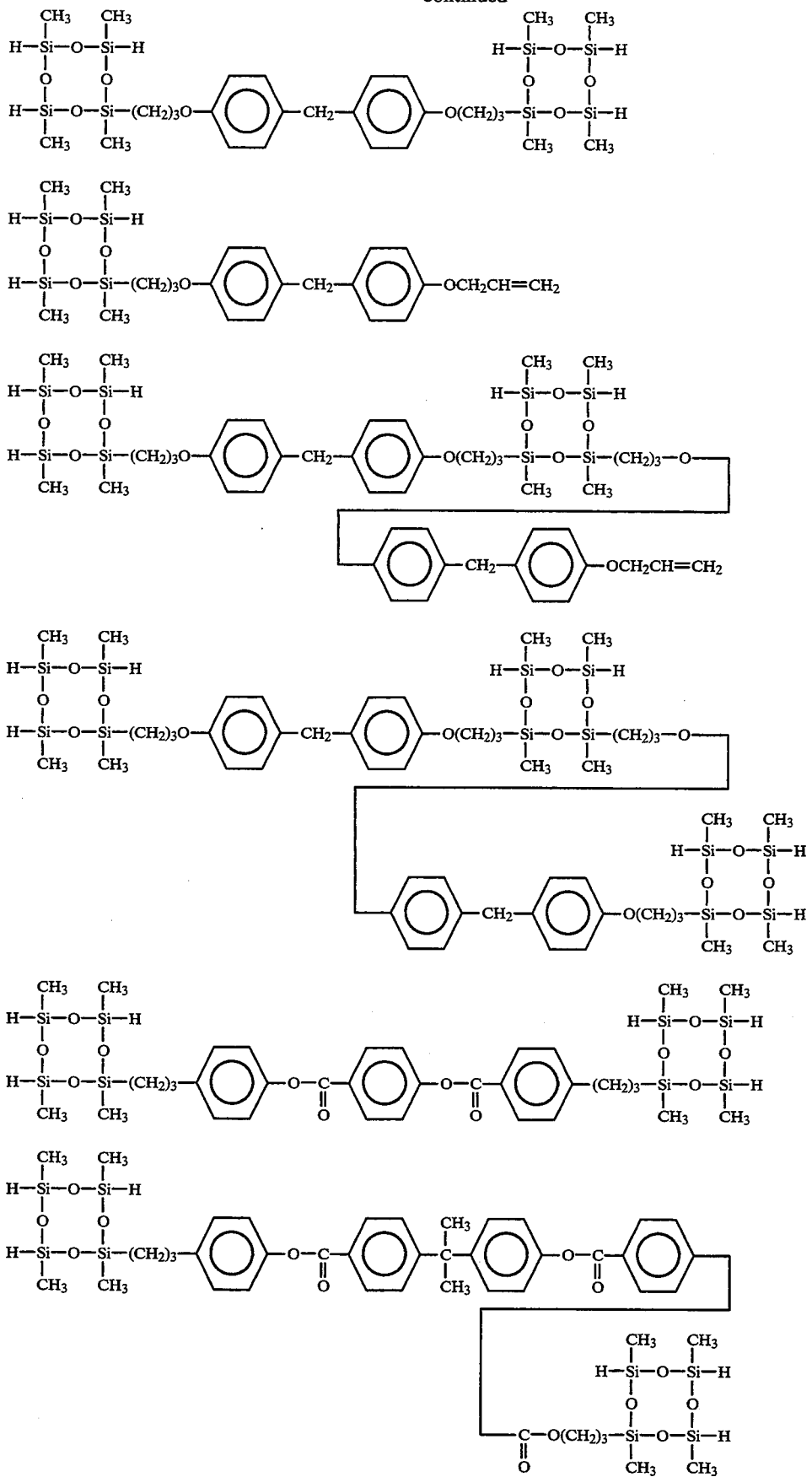

-continued

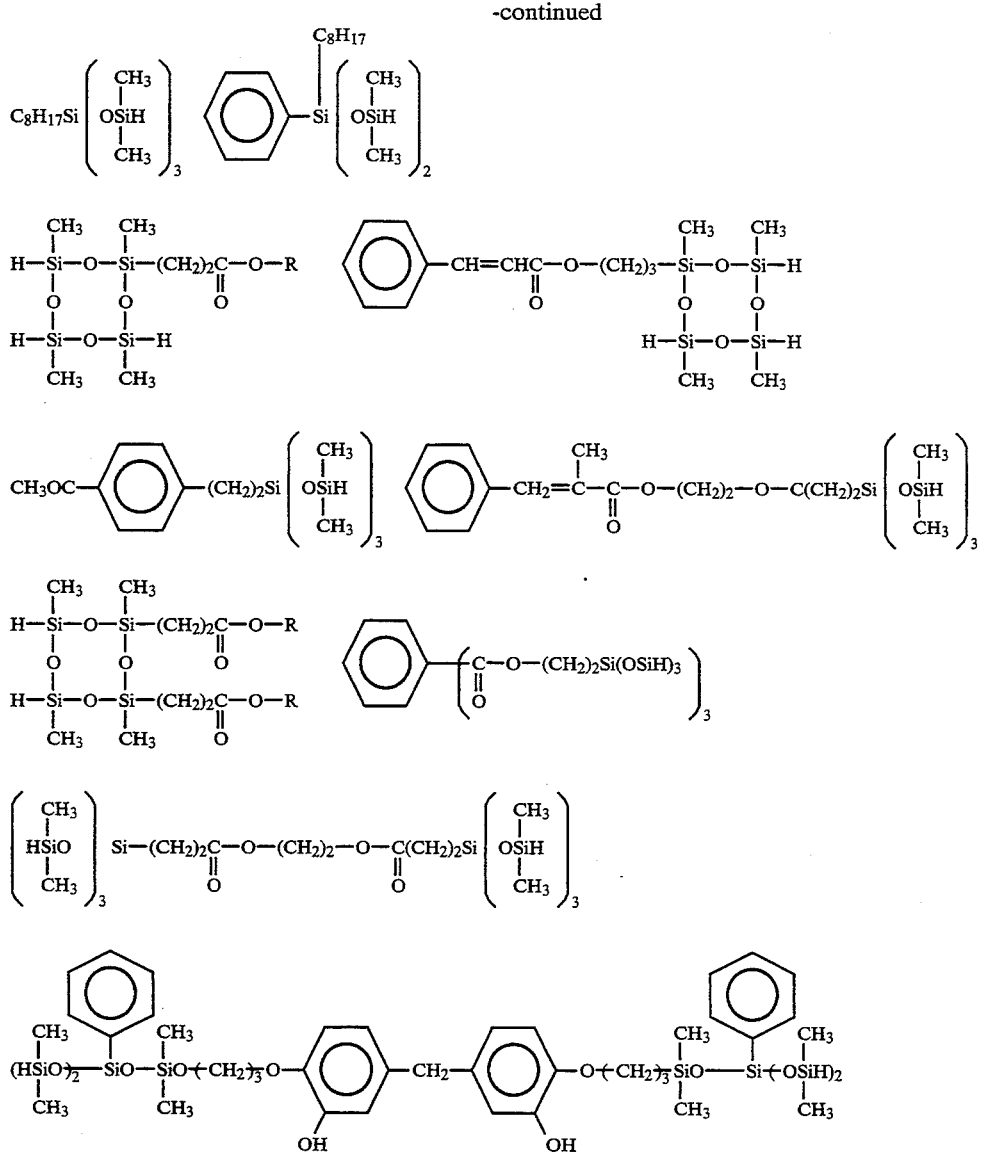

The amount of the adhesive agent blended in a silicone rubber composition is properly determined without undue experimentation, although about 0.01 to 50 parts by weight, more preferably about 0.1 to 5 parts by weight per 100 parts by weight of an alkenyl group-bearing organopolysiloxane, which will be later described as component (a), is preferred. Less than 0.01 part of the adhesive agent is too small to provide adherence to the adhered organic resin, whereas more than 50 parts of the adhesive agent would deteriorate the physical properties of silicone rubber and rather promote adhesion to metals.

The adhesive silicone rubber composition of the invention is an addition reaction curing type silicone rubber composition containing the adhesive agent as an essential component. In addition to the adhesive agent, the composition may contain conventional components which are commonly used in conventional silicone rubber compositions.

In addition to the adhesive agent, the adhesive silicone rubber composition of the invention generally includes (a) an alkenyl group-containing organopolysiloxane, (b) an organohydrogenpolysiloxane, and (c) an addition reaction catalyst.

Component (a) is an organopolysiloxane containing an alkenyl group which may be selected from well-known organopolysiloxanes conventionally used as a major component of addition reaction curing type silicone rubber compositions, typically having a viscosity of about 100 to 100,000 centipoise at room temperature.

Preferred organopolysiloxanes are represented by the general formula: $R_aSiO_{(4-a)/2}$ wherein R is a substituted or unsubstituted monovalent hydrocarbon group, preferably having 1 to 8 carbon atoms. Examples of the hydrocarbon group represented by R include alkyl groups such as methyl, ethyl and propyl; alkenyl groups such as vinyl, propenyl and butenyl; aryl groups such as phenyl and xylyl; and halo- or cyano-substituted hydrocarbon groups such as 3,3,3-trifluoropropyl. The monovalent hydrocarbon groups may be identical or different as long as an alkenyl group is contained in the organopolysiloxane molecule. The content of alkenyl group is preferably 0.01 to 10 mol %, especially 0.1 to 1 mol % of the entire R groups. Letter a is a number of 1.9 to 2.4. The organopolysiloxane may be a linear one or a branched one further containing a $RSiO_{3/2}$ unit or $SiO_{4/2}$ unit. The substituent on the silicon atom is basically any of the above-mentioned groups. It is desirable to introduce a vinyl group among the alkenyl groups and a methyl or phenyl group among other substituent groups.

Illustrative, non-limiting examples of the organopolysiloxane are given below.

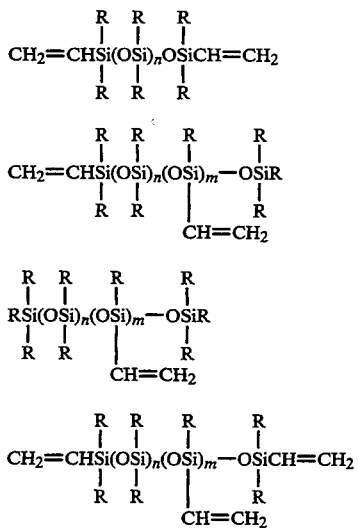

In these formulae, R is as defined above (excluding an aliphatic unsaturated group), and letters m and n are positive numbers meeting $m+n=100$ to 5000 and $m/(m+n)=0.001$ to 0.1.

The organopolysiloxanes may be prepared by per se known methods. For example, they are obtained by effecting equilibration reaction between an organocyclopolysiloxane and a hexaorganodisiloxane in the presence of an alkali or acid catalyst.

Component (b) is an organohydrogenpolysiloxane which is used as a curing agent in conventional addition reaction curing type silicone rubber compositions. The organohydrogenpolysiloxane (b) serves as a cross-linking agent by reacting with component (a). It is not particularly limited in molecular structure and may be any of conventionally used organohydrogenpolysiloxanes of linear, cyclic and branched structures. However, it should have at least two hydrogen atoms each directly attached to a silicon atom in a molecule. The substituent or substituents attached to a silicon atom other than hydrogen are the same as the substitutents described for organopolysiloxane (a).

Component (b) is preferably added in an amount to provide 0.4 to 5 equivalents, especially 0.8 to 2 equivalents per alkenyl group in component (a). Less than 0.4 equivalents of component (b) on this basis would result in cured silicone rubber having too low crosslinking density and hence, less heat resistance. More than 5 equivalents of component (b) would give rise to a bubbling problem due to a dehydrogenation reaction, which would also adversely affect heat resistance.

The organohydrogenpolysiloxanes may be prepared by per se known methods. For example, the most commonly used method is by equilibrating octamethylcyclotetrasiloxane and/or tetramethylcyclotetrasiloxane and a compound containing a hexamethyldisiloxane or 1,1-dihydro-2,2,3,3-tetramethyldisiloxane unit, which will become a terminal group in the presence of a catalyst such as sulfuric acid, trifluoromethanesulfonic acid, and methanesulfonic acid, at a temperature between $-10°$ C. and $+40°$ C.

Component (c) is an addition reaction catalyst which is generally selected from platinum, platinum compounds, rhodium and rhodium compounds. Since the catalyst is used for promoting curing addition reaction or hydrosilation between components (a) and (b), it may be a conventional known one. Exemplary are platinum black, chloroplatinic acid, alcohol modified chloroplatinic acid, complexes of chloroplatinic acid with olefins, aldehydes, vinylsiloxanes or acetylene alcohols, and rhodium complexes. The amount of the catalyst added is suitably determined in accordance with a desired curing rate although it is generally in the range of 0.1 to 1000 ppm, preferably 1 to 200 ppm of platinum or rhodium based on the total of the entire components.

In one preferred embodiment where the silicone rubber should have physical strength, the silicone rubber composition further includes finely divided silica having a specific surface area of at least 50 $m^2/g$ in an amount of 0 to 100 parts, preferably 5 to 50 parts, more preferably 10 to 40 parts by weight per 100 parts by weight of the total of components (a) and (b). Exemplary of hydrophilic silica are Aerosil 130, 200 and 300 (commercially available from Nippon Aerosil K.K. and Degussa), Cabosil MS-5 and MS-7 (Cabot Corp.), Rheorosil QS-102 and 103 (Tokuyama Soda K.K.), and Nipsil LP (Nippon Silica K.K.). Exemplary of hydrophobic silica are Aerosil R-812, R-812S, R-972 and R-974 (Degussa), Rheorosil MT-10 (Tokuyama Soda K.K.), and Nipsil SS series (Nippon Silica K.K.).

In some cases, the curing time of the silicone rubber composition must be controlled in order that it be effective in practice. Then a suitable control agent is used. It may be selected from vinyl-containing organopolysiloxanes such as vinylcyclotetrasiloxane, triallylisocyanurate, alkyl maleates, acetylene alcohols and silane or siloxane modified derivatives thereof, hydroperoxides, tetramethylethylenediamine, benzotriazole and mixtures thereof. Also useful are platinum group compounds combined with organic resins and silicone resins.

Moreover, suitable additives may be blended in the silicone rubber composition. Such additives include non-reinforcing fillers such as ground quartz, diatomaceous earth, calcium carbonate, coloring agents including inorganic pigments such as Cobalt Blue and organic dyes, agents for improving heat resistance and flame retardance such as cerium oxide, zinc carbonate, manganese carbonate, iron oxide, titanium oxide, and carbon black.

The composition of the invention is advantageously used to join with organic resins, especially thermoplastic resins to form one-piece articles. Examples of the thermoplastic resin to which the composition can be joined include polypropylene, polyethylene, ABS resins, nylon, polycarbonate, polyphenylene oxide, polybutylene terephthalate, polyphenylene sulfide, polyethylene terephthalate, acrylic resins, polyacetal resins, and other engineering plastics such as polyarylates, polysulfones, polyether sulfones, polyether imides, polyether ether ketones, polyimides, and liquid crystal polymers.

As long as a suitable adhesive agent is selected in accordance with a particular adhered thermoplastic resin by considering its wettability to the resin, there is obtained a silicone rubber composition which adheres well to the thermoplastic resin, although the adhesive agent is free of a functional group except for a hydrogen atom directly attached to a silicon atom. That is, the adhesive agent according to the present invention permits the silicone rubber composition to exert selective adhesion to organic resins to which conventional silicone rubber compositions were regarded impossible to join firmly, while suppressing adhesion to metals, typically metallic molds.

The thermoplastic resin to which the silicone rubber composition is to be joined may take various shapes in common solid state, although resin materials loaded with glass fiber reinforcements, silica reinforcements and other inorganic reinforcements are advantageous to form a more reliable adhesion. The glass fibers may be those commonly used in resin reinforcement. The silica reinforcements include crystalline and amorphous silica powders. Other inorganic reinforcements include metal fibers such as brass fibers, nickel fibers, stainless steel fibers, and aluminum fibers as well as mica, talc, clay, kaolin, aluminum hydroxide, silicon carbide whiskers, calcium sulfate, and calcium carbonate.

Better adhesion is achieved when such fillers have been treated with substances having an unsaturated group such as vinyl-containing silazanes, siloxasilazanes, vinylalkoxysilanes, and vinyl-containing silicone resins. For improving adhesion to a thermoplastic resin, it is also effective to introduce into or add to the thermoplastic resin a component having an unsaturated group. In introducing into or adding to the adhered thermoplastic resin a component having an unsaturated group, it is necessary that the unsaturated group be present at the time of adhesion. Little of such benefit is observed when a compound having an aliphatic unsaturated group and a hydrolysable group attached to a silicon atom is grafted to an olefinic resin so that the unsaturated group is substantially consumed as disclosed in JP-A 183843/1988.

Examples of the adhered thermoplastic resin which is modified by introducing or adding a compound having an unsaturated group include polycarbonate resins terminally modified with an aliphatic unsaturated group such as a vinyl, allyl or methacryl group; polyethylene and polypropylene modified with an aliphatic unsaturated group at a side chain as disclosed in JP-A 269110/1990; acrylic resins modified with an allyl ester group or vinyl dimethyl silyl group at a side chain; and polyamide resins having an aliphatic unsaturated group substituted on a nitrogen atom. Also useful are dispersions in various resins of unsaturated group-containing compounds such as triallyl isocyanurate, triallyl trimellitate, unsaturated group-containing polybutadiene oligomers, oligomers of unsaturated group-containing compounds, and unsaturated group-containing silicone resins or polymers.

There have been described adhesive silicone rubber compositions which provide improved adhesion to organic resins, but minimum adhesion to metals so that they may be used in producing composite articles of integrated silicone rubber and organic resins using molds.

EXAMPLE

Examples of the present invention are given below by way of illustration and not by way of limitation. All parts are by weight.

Examples 1-4

Preparation of Silicone Rubber Composition

A kneader was charged with 100 parts of a dimethylsiloxane polymer blocked with a dimethylvinylsilyl group at either end and having a viscosity of 10,000 centipoise at 25° C., 40 parts of fumed silica having a specific surface area of 300 cm²/g, 8 parts of hexamethyldisilazane, and 1 part of water. The contents were agitated and mixed at room temperature for one hour, heated to 150° C., and mixed for a further 2 hours at the temperature. Thereafter, the mixture was cooled down to room temperature. To the mixture were added 20 parts of the dimethylsiloxane polymer blocked with a dimethylvinylsilyl group at either end and having a viscosity of 10,000 centipoise at 25° C., 3 parts of a methylhydrogenpolysiloxane represented by formula (i) below and having a viscosity of about 10 centipoise at 25° C., 4 parts of a vinylmethylpolysiloxane containing 5 mol % of a vinyl group directly attached to a silicon atom and having a viscosity of 1,000 centipoise at 25° C., 0.1 part of acetylene alcohol for extending the curing time at room temperature, and 50 ppm calculated as platinum atom of a platinum vinylsiloxane complex. The mixture was fully mixed until uniform, obtaining a liquid addition type silicone rubber composition (S).

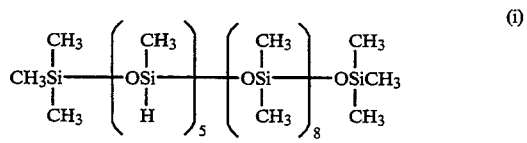
(i)

Composition (S) was pressed into a sheet at 120° C. for 10 minutes. Upon measurement of mechanical properties, the sheet had a hardness of 40 on JIS A scale, an elongation of 500%, a tensile strength of 100 kgf/cm², and a tear strength of 35 kgf/cm.

To 100 parts of silicone rubber composition (S) was added 0.5 or 1 part of a compound of formula (ii) or (iii) shown below as the adhesive agent. There were obtained four silicone rubber compositions within the scope of the invention.

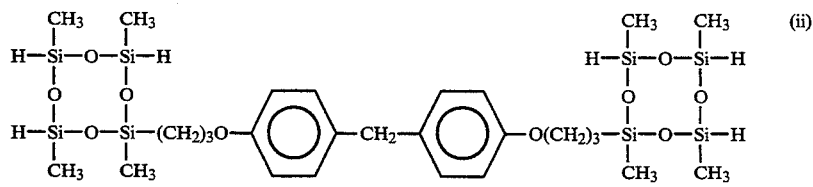
(ii)

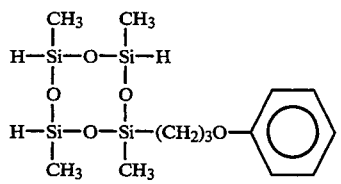

(iii)

Using these four silicone rubber compositions, the following tests were carried out.

Test 1

A polyether ether ketone resin (PEEK) was admitted into a thermoplastic resin injection molding machine where the resin was plasticized at 360° C. and injected into a plurality of sheet-shaped mold cavities whereby a plurality of sheets of 25 mm wide, 100 mm long, and 2 mm thick were molded. The injection molding conditions included an injection time of 15 seconds, a cooling time of 10 seconds, an injection pressure of 1,200 kg/cm$^2$, a clamping pressure of 35 ton, and a cavity temperature of 140° C.

A polyether sulfone resin (PES) was similarly admitted into the injection molding machine. A plurality of sheets of the same dimensions were molded. The molding conditions included a plasticizing temperature of 340° C., an injection time of 10 seconds, a cooling time of 30 seconds, an injection pressure of 1,250 kg/cm$^2$, a clamping pressure of 35 ton, and a cavity temperature of 140° C.

A polyether imide resin (PEI) was similarly admitted into the injection molding machine. A plurality of sheets of the same dimensions were molded. The molding conditions included a plasticizing temperature of 360° C., an injection time of 15 seconds, a cooling time of 30 seconds, an injection pressure of 1,000 kg/cm$^2$, a clamping pressure of 35 ton, and a cavity temperature of 90° C.

To a jig for forming shear adhesion test pieces was fixedly attached each of the resin sheets or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in the side and plan views of FIGS. 1A and 1B. In FIG. 1, a resin or metal sheet 1 is joined to a cured part of the silicone composition 2 (25×100×2 mm) through a bond zone 3. Supports 4 and 5 support the resin or metal sheet 1 and the cured silicone part 2, respectively. The test pieces were examined by an adhesion test. The results are shown in Table 1.

Using an automatic contact angle meter (manufactured by Kyowa Kaimen Kagaku K.K.), the adhesive agents (ii) and (iii) were measured for contact angle on the polyether ether ketone, polyether sulfon and polyether imide resin sheets. The results are shown in Table 2.

TABLE 1

| | Example | | | |
|---|---|---|---|---|
| | 1 | 2 | 3 | 4 |
| Adhesive agent (ii) | 0.5 pbw | 1 pbw | — | — |
| Adhesive agent (iii) | — | — | 0.5 pbw | 1 pbw |
| Adhered | | | | |
| Cr-plated metal | peeled | peeled | peeled | peeled |
| Ni-plated metal | peeled | peeled | peeled | peeled |
| Al alloy | peeled | peeled | peeled | peeled |
| PEEK | bonded | bonded | bonded | bonded |
| PES | bonded | bonded | bonded | bonded |
| PEI | bonded | bonded | bonded | bonded |

TABLE 2

| | Contact angle ($\theta$) | |
|---|---|---|
| | Adhesive Agent (ii) | Adhesive Agent (iii) |
| PEEK | 48.0° | 28.7° |
| PES | 49.1° | 30.1° |
| PEI | 48.2° | 30.5° |

Test 2

A terminally allyl-modified polycarbonate resin (PC) was admitted into a thermoplastic resin injection molding machine where the resin was plasticized at 290° C. and injected into a plurality of sheet-shaped mold cavities whereby a plurality of sheets of 25 mm wide, 100 mm long, and 2 mm thick were molded. The injection molding conditions included an injection time of 6 seconds, a cooling time of 30 seconds, an injection pressure of 1,000 kg/cm$^2$, a clamping pressure of 35 ton, and a cavity temperature of 100° C.

To a jig for forming shear adhesion test pieces was fixedly attached the resin sheet or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in FIG. 1. The test pieces were examined by an adhesion test. The results are shown in Table 3.

Using the automatic contact angle meter used in Test 1, the adhesive agents (ii) and (iii) were measured for contact angle on the polycarbonate resin sheet. The results are shown in Table 4.

TABLE 3

| | Example | | | |
|---|---|---|---|---|
| | 1 | 2 | 3 | 4 |
| Adhesive agent (ii) | 0.5 pbw | 1 pbw | — | — |
| Adhesive agent (iii) | — | — | 0.5 pbw | 1 pbw |
| Adhered | | | | |
| Cr-plated metal | peeled | peeled | peeled | peeled |
| Ni-plated metal | peeled | peeled | peeled | peeled |
| Al alloy | peeled | peeled | peeled | peeled |
| modified PC | bonded | bonded | bonded | bonded |

TABLE 4

| | Contact angle ($\theta$) | |
|---|---|---|
| | Adhesive Agent (ii) | Adhesive Agent (iii) |
| modified PC | 35.9° | 10.0° |

Test 3

A polybutyrene terephthalate resin (PBT) loaded with 30% by weight of glass fibers was admitted into a thermoplastic resin injection molding machine where the resin was plasticized at 240° C. and injected into a plurality of sheet-shaped mold cavities whereby a plurality of sheets of 25 mm wide, 100 mm long, and 2 mm thick were molded. The injection molding conditions included an injection time of 15 seconds, a cooling time of 10 seconds, an injection pressure of 75 kg/cm², a clamping pressure of 35 ton, and a cavity temperature of 60° C.

A polycarbonate resin (PC) loaded with 10% by weight of glass fibers was similarly admitted into the injection molding machine. A plurality of sheets of the same dimensions were molded. The molding conditions included a plasticizing temperature of 290° C., an injection time of 10 seconds, a cooling time of 30 seconds, an injection pressure of 1,000 kg/cm², a clamping pressure of 35 ton, and a cavity temperature of 100° C.

An acrylonitrile-butadiene-styrene resin (ABS) loaded with 15% by weight of glass fibers was similarly admitted into the injection molding machine. A plurality of sheets of the same dimensions were molded. The molding conditions included a plasticizing temperature of 220° C., an injection time of 15 seconds, a cooling time of 30 seconds, an injection pressure of 800 kg/cm², a clamping pressure of 35 ton, and a cavity temperature of 50° C.

To a jig for forming shear adhesion test pieces was fixedly attached each of the resin sheets or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in FIG. 1. The test pieces were examined by an adhesion test. The results are shown in Table 5.

Using automatic contact angle meter in Test 1, adhesive agents components (ii) and (iii) were measured for contact angle on the glass fiber-reinforced polybutyrene terephthalate, polycarbonate and ABS resin sheets. The results are shown in Table 6.

TABLE 5

|  | Example |  |  |  |
|---|---|---|---|---|
|  | 1 | 2 | 3 | 4 |
| Adhesive agent (ii) | 0.5 pbw | 1 pbw | — | — |
| Adhesive agent (iii) | — | — | 0.5 pbw | 1 pbw |
| Adhered |  |  |  |  |
| Cr-plated metal | peeled | peeled | peeled | peeled |
| Ni-plated metal | peeled | peeled | peeled | peeled |
| Al alloy | peeled | peeled | peeled | peeled |
| reinforced PBT | bonded | bonded | bonded | bonded |
| reinforced PC | bonded | bonded | bonded | bonded |
| reinforced ABS | bonded | bonded | bonded | bonded |

TABLE 6

|  | Contact angle ($\theta$) | |
|---|---|---|
|  | Adhesive Agent (ii) | Adhesive Agent (iii) |
| reinforced PBT | 40.3° | 18.70 |
| reinforced PC | 39.1° | 20.1° |

TABLE 6-continued

|  | Contact angle ($\theta$) | |
|---|---|---|
|  | Adhesive Agent (ii) | Adhesive Agent (iii) |
| reinforced ABS | 38.3° | 20.5° |

Test 4

To 100 parts of unreinforced polycarbonate resin was added 5 or 10 parts of silica treated with vinyl-containing silazane. Each silica-loaded resin was kneaded in a kneader/extruder at 270° C. for 10 minutes and extruded thereby into strands which were pelletized by means of a rotary cuter.

The silica-loaded polycarbonate resin was admitted into a thermoplastic resin injection molding machine where the resin was plasticized at 290° C. and injected into a plurality of sheet-shaped mold cavities whereby a plurality of sheets of 25 mm wide, 100 mm long, and 2 mm thick were molded. The injection molding conditions included an injection time of 6 seconds, a cooling time of 30 seconds, an injection pressure of 1,000 kg/cm², a clamping pressure of 35 ton, and a cavity temperature of 100° C.

To a jig for forming shear adhesion test pieces was fixedly attached the resin sheet or each of chromium-plated metal, nickel-plated metal and aluminum alloy sheets of the same dimensions. A proper amount of the silicone rubber composition was poured into the jig where it was cured by heating for 8 minutes in a 120° C. constant temperature over, obtaining a test piece as shown in FIG. 1. The test pieces were examined by an adhesion test. The results are shown in Table 7.

Using the automatic contact angle meter in Test 1, adhesive agents components (ii) and (iii) were measured for contact angle on the silica-loaded polycarbonate resin sheets. The results are shown in Table 8.

TABLE 7

|  | Example |  |  |  |
|---|---|---|---|---|
|  | 1 | 2 | 3 | 4 |
| Adhesive agent (ii) | 0.5 pbw | 1 pbw | — | — |
| Adhesive agent (iii) | — | — | 0.5 pbw | 1 pbw |
| Adhered |  |  |  |  |
| Cr-plated metal | peeled | peeled | peeled | peeled |
| Ni-plated metal | peeled | peeled | peeled | peeled |
| Al alloy | peeled | peeled | peeled | peeled |
| Silica-loaded PC |  |  |  |  |
| 5 pbw | bonded | bonded | bonded | bonded |
| 10 pbw | bonded | bonded | bonded | bonded |

TABLE 8

|  | Contact angle ($\theta$) | |
|---|---|---|
|  | Adhesive Agent (ii) | Adhesive Agent (iii) |
| 5 pbw silica-loaded PC | 25.9° | 20.0° |
| 10 pbw silica-loaded PC | 36.0° | 29.2° |

Examples 5–6

To 100 parts of silicone rubber composition (S) in Examples 1–4 was added 0.5 or 1 part of a compound of formula (iv) shown below as the adhesive agent. There were obtained two silicone rubber compositions within the scope of the invention.

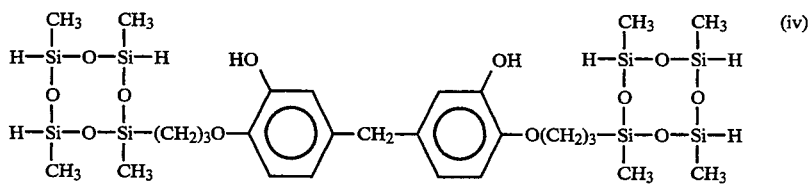

(iv)

Using these two silicone rubber compositions, the following tests were carried out.

Test 5

A nylon-66 resin was admitted into a thermoplastic resin injection molding machine where the resin was plasticized at 280° C. and injected into a plurality of sheet-shaped mold cavities whereby a plurality of sheets of 25 mm wide, 100 mm long, and 2 mm thick were molded. The injection molding conditions included an injection time of 6 seconds, a cooling time of 20 seconds, an injection pressure of 800 kg/cm², a clamping pressure of 35 ton, and a cavity temperature of 80° C.

To a jig for forming shear adhesion test pieces was fixedly attached the resin sheet or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in FIG. 1. The test pieces were examined by an adhesion test. The results are shown in Table 9.

Using the automatic contact angle meter in Test 1, the adhesive agent (iv) was measured for contact angle on the nylon-66 resin sheets. The results are shown in Table 10.

TABLE 9

|  | Example | |
|---|---|---|
|  | 5 | 6 |
| Adhesive agent (iv) | 0.5 pbw | 1 pbw |
| Adhered |  |  |

TABLE 9-continued

|  | Example | |
|---|---|---|
|  | 5 | 6 |
| Cr-plated metal | peeled | peeled |
| Ni-plated metal | peeled | peeled |
| Al alloy | peeled | peeled |
| Nylon-66 | bonded | bonded |

TABLE 10

|  | Contact angle (θ) Adhesive Agent (iv) |
|---|---|
| Nylon-66 | 25.0° |

Examples 7-12

To 100 parts of silicone rubber composition (S) in Examples 1-4 was added 0.5 or 1 part of a compound of formula (v), (vi) or (vii) shown below as the adhesive agent. There were obtained six silicone rubber compositions within the scope of the invention.

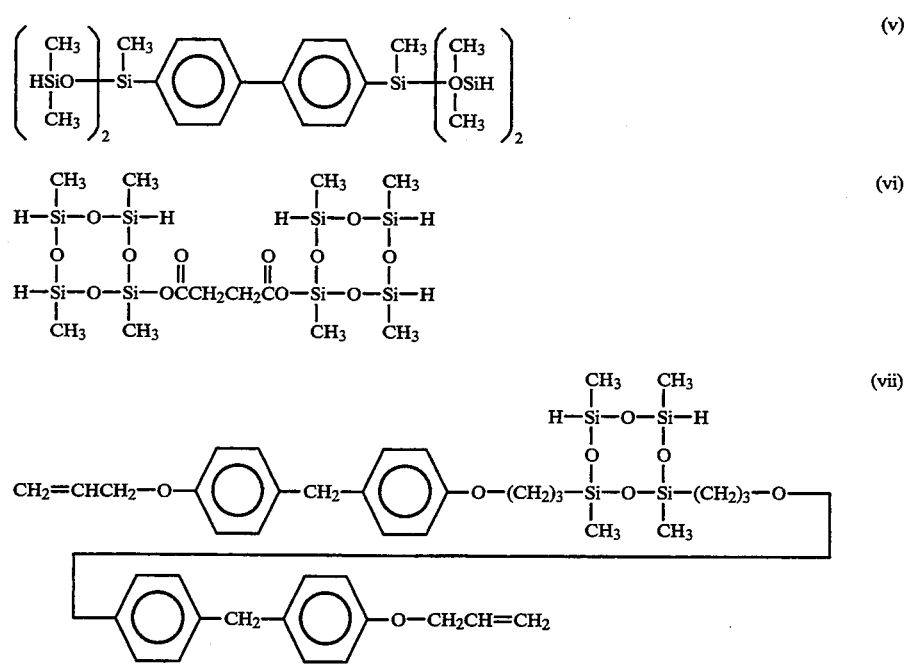

Using these six silicone rubber compositions, the following tests were carried out.

Test 6

A nylon-66 resin loaded with 30% by weight of glass fibers was admitted into a thermoplastic resin injection molding machine where the resin was plasticized at 270° C. and injected into a plurality of sheet-shaped mold cavities whereby a plurality of sheets of 25 mm wide, 100 mm long, and 2 mm thick were molded. The injection molding conditions included an injection time of 15 seconds, a cooling time of seconds, an injection silicone rubber compositions outside the scope of the invention.

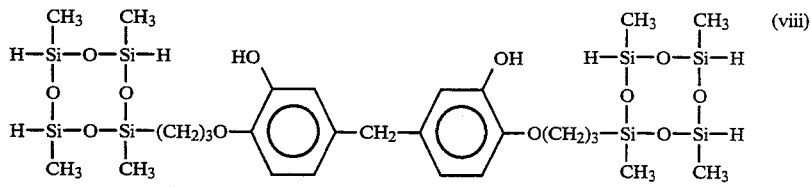

pressure of 800 kg/cm², a clamping pressure of 35 ton, and a cavity temperature of 80° C.

Similarly, a polyethylene terephthalate resin (PET) loaded with 30% by weight of glass fibers was admitted into the injection molding machine. A plurality of sheets of the same dimensions were molded. The molding conditions included a plasticizing temperature of 270° C., an injection time of 10 seconds, a cooling time of 30 seconds, an injection pressure of 600 kg/cm², a clamping pressure of 35 ton, and a cavity temperature of 100° C.

Similarly, a polyphenylene oxide resin (PPO) loaded with 20% by weight of glass fibers was admitted into the injection molding machine. A plurality of sheets of the same dimensions were molded. The molding conditions included a plasticizing temperature of 270° C., an injection time of 10 seconds, a cooling time of 30 seconds, an injection pressure of 1,000 kg/cm², a clamping pressure of 35 ton, and a cavity temperature of 100° C.

To a jig for forming shear adhesion test pieces was fixedly attached each of the resin sheets or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in FIG. 1. The test pieces were examined by an adhesion test. The results are shown in Table 11.

TABLE 11

| | Example | | | | | |
|---|---|---|---|---|---|---|
| | 7 | 8 | 9 | 10 | 11 | 10 |
| Adhesive agent (v) | 0.5 | 1 | — | — | — | — |
| Adhesive agent (vi) | — | — | 0.5 | 1 | — | — |
| Adhesive agent (vii) | — | — | — | — | 0.5 | 1 |
| Adhered | | | | | | |
| Cr-plated metal | peeled | peeled | peeled | peeled | peeled | peeled |
| Ni-plated metal | peeled | peeled | peeled | peeled | peeled | peeled |
| Al alloy | peeled | peeled | peeled | peeled | peeled | peeled |
| Fiber-reinforced nylon 66 | bonded | bonded | bonded | bonded | bonded | bonded |
| Fiber-reinforced PET | bonded | bonded | bonded | bonded | bonded | bonded |
| Fiber-reinforced PPO | bonded | bonded | bonded | bonded | bonded | bonded |

Comparative Examples 1–2

To 100 parts of silicone rubber composition (S) in Examples 1–4 was added 0.5 or 1 part of a compound of formula (viii) shown below. There were obtained two silicone rubber compositions outside the scope of the invention.

To a jig for forming shear adhesion test pieces was fixedly attached each of the polyether ether ketone, polyether sulfone, and polyether imide resin sheets prepared as in the foregoing Examples. A proper amount of the silicone rubber composition was poured into the jig where it was cured by heating for 8 minute in a 120° C. constant temperature oven, obtaining a test piece as shown in FIG. 1. The test pieces were examined by an adhesion test to find that the silicone rubber was readily peeled from each resin sheet.

The compound (viii) had a contact angle of 75.0°, 72.5° and 78.0° on the polyether ether ketone, polyether sulfone, and polyether imide resin sheets, respectively.

Comparative Example 3

To 100 parts of silicone rubber composition (S) in Examples 1–4 was added 2 parts of a compound of formula (ix) or (x) shown below. There were obtained two silicone rubber compositions outside the scope of the invention.

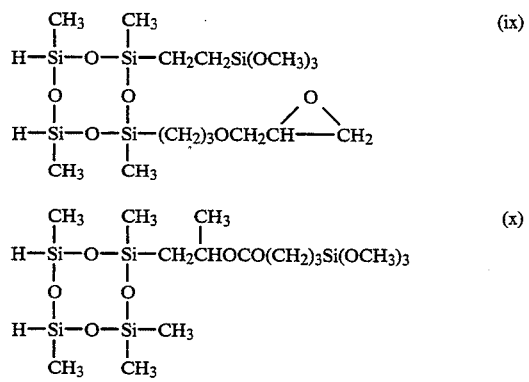

A polypropylene resin modified with 1.5 mol % of a diene compound as described in JP-A 269110/1990 was admitted into a thermoplastic resin injection molding machine where the resin was plasticized at 200° C. and injected into a plurality of sheet-shaped mold cavities whereby a plurality of sheets of 25 mm wide, 100 mm long, and 2 mm thick were molded. The injection molding conditions included an injection time of 6 seconds, a cooling time of 30 seconds, an injection pressure of 1,000 kg/cm², a clamping pressure of 35 ton, and a cavity temperature of 60° C.

To a jig for forming shear adhesion test pieces was fixedly attached the resin sheet or each of chromium-plated metal, nickel-plated metal and aluminum alloy sheets of the same dimensions. A proper amount of the silicone rubber composition was poured into the jig where it was cured by heating for 8 minutes in a 120° C. constant temperature oven, obtaining a test piece as shown in FIG. 1. The test pieces were examined by an adhesion test. The results are shown in Table 12.

Using the automatic contact angle meter in Test 1, the adhesive agents (ix) and (x) were measured for contact angle on the modified polypropylene resin sheet. The results are shown in Table 13.

TABLE 12

| | Comparative Example 3 |
|---|---|
| Modified PP | bonded |
| Cr-plated metal | bonded |
| Ni-plated metal | bonded |
| Aluminum alloy | bonded |

TABLE 13

| | Contact angle (θ) | |
|---|---|---|
| | Adhesive Agent (ix) | Adhesive Agent (x) |
| Modified | 24.1° | 15.0° |

Although some preferred embodiments have been described, many modifications and variations may be made thereto in the light of the above teachings. It is therefore to be understood that within the scope of the appended claims, the invention may be practiced otherwise than as specifically described.

We claim:

1. An adhesive silicone rubber composition of addition reaction curing type comprising (a) an organopolysiloxane containing an alkenyl group; (b) an organohydrogenpolysiloxane having at least two hydrogen atoms directly attached to a silicon atom in a molecule; (c) an addition reaction catalyst; and (d) an adhesive agent selected from compounds of the following formulae (I), (II) and (III):

$$A—(D—B)_x—D—A \quad (I)$$

$$C—(B—D)_x—B—C \quad (II)$$

$$A—E \quad (III)$$

wherein each of A and B is a silane or siloxane group, each group having at least one hydrogen atom directly attached to a silicon atom and an optional substituent which is a substituted or unsubstituted monovalent hydrocarbon group having 1 to 8 carbon atoms attached to the same or different silicon atom, A being monovalent and B being divalent, each of C and D is a group having contained therein at least one member selected from the group consisting of a substituted or unsubstituted aryl group, a substituted or unsubstituted arylene group,

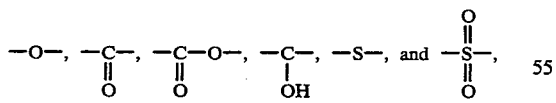

and an optional substituent which is selected from alkyl or alkylene groups, C being monovalent and D being divalent, E is a monovalent group as defined for C, with the proviso that the total number of atoms in E other than hydrogen and halogen atoms is at least 8, and letter x is 0 or a positive number, said adhesive silicone rubber composition giving a cured product that does not adhere to metal.

2. The adhesive silicone rubber composition of claim 1, wherein said at least one member contained in the groups represented by C, D and E is selected from the following formulae (1) to (10):

(1)

(2)

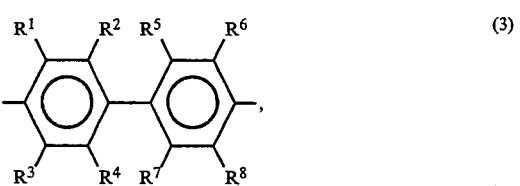

(3)

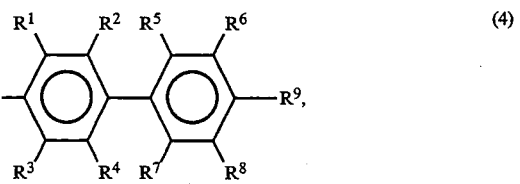

(4)

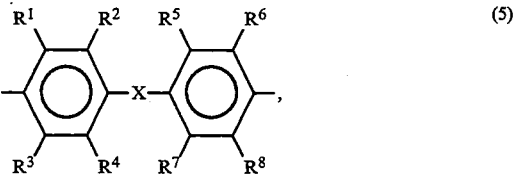

(5)

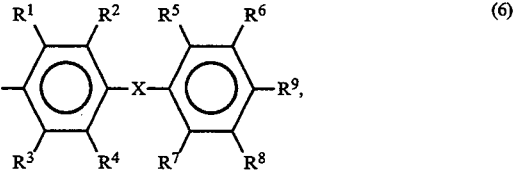

(6)

(7)

(8)

(9)

and

(10)

wherein each of $R^1$ to $R^9$, which may be identical or different, is a monovalent group selected from the group consisting of a hydrogen atom, halogen atom, hydroxyl group, substituted or unsubstituted monovalent hydrocarbon group, and alkoxy groups;

X is a divalent group selected from the group consisting of

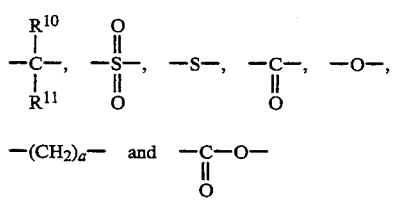

wherein each of $R^{10}$ and $R^{11}$, which may be identical or different, is a monovalent group selected from the group consisting of a hydrogen atom, halogen atom, and substituted or unsubstituted monovalent hydrocarbon group, or $R^{10}$ and $R^{11}$ taken together form a carbocyclic or heterocyclic ring, and letter "a" is an integer of at least 2.

3. The composition of claim 1 or 2 wherein said compound has a contact angle of up to 70° on an organic resin to which the composition is to be joined.

4. The adhesive silicone rubber composition according to claim 1, wherein the adhesive agent is at least one compound selected from the group consisting of

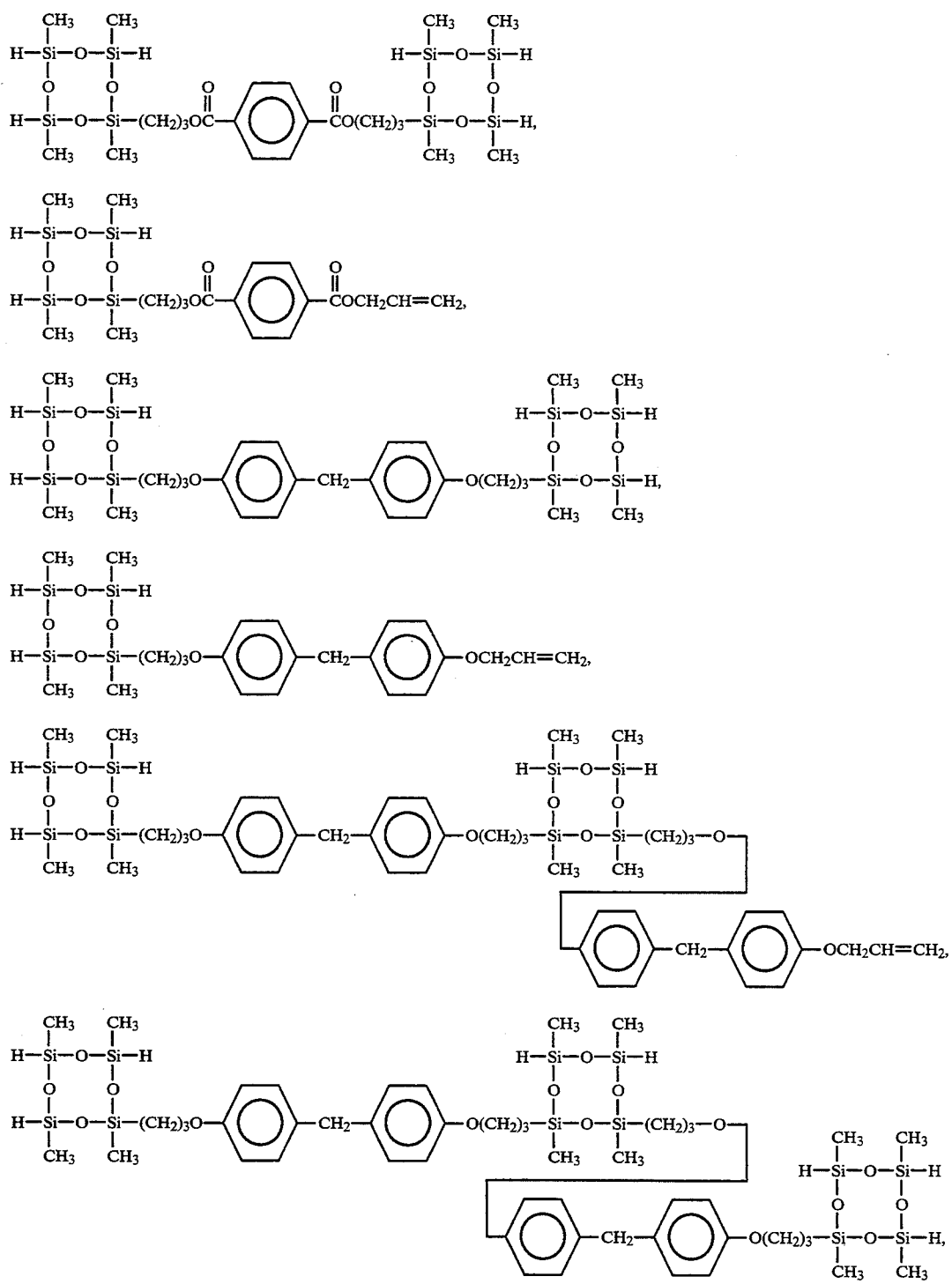

-continued
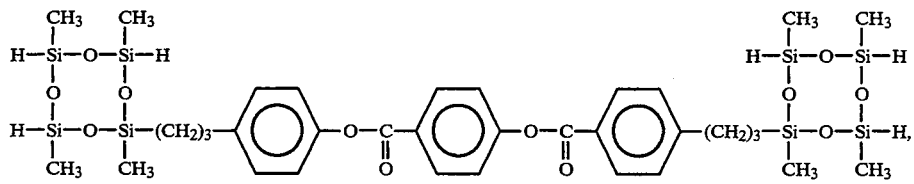
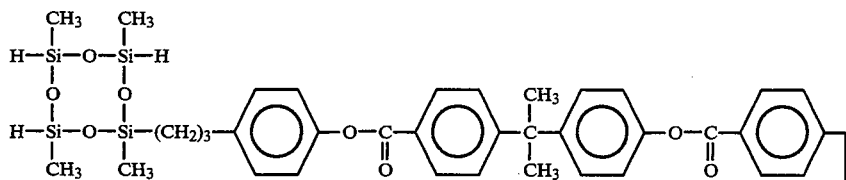
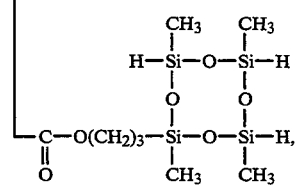
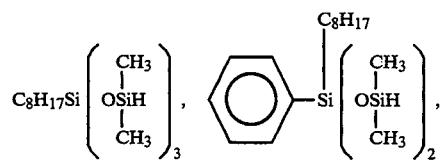
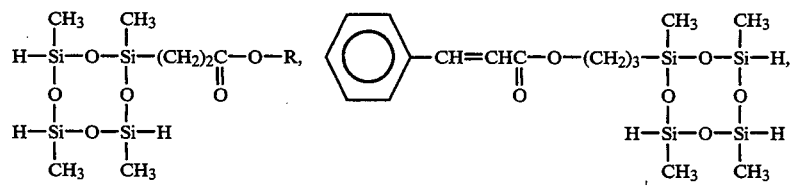
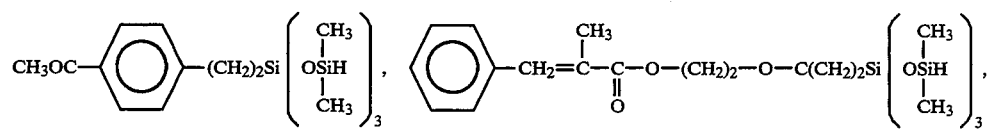
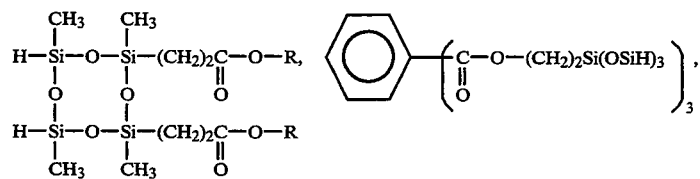
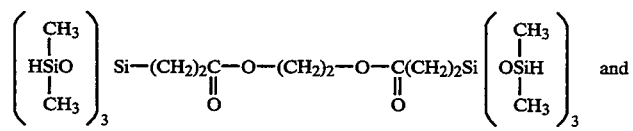 and

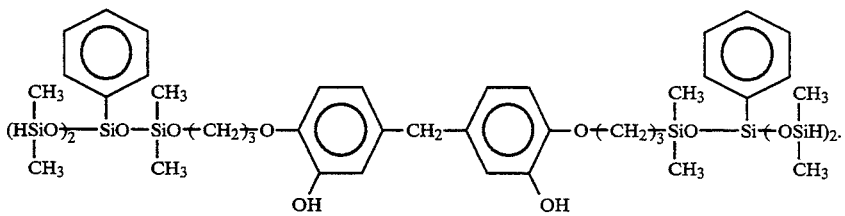

5. The adhesive rubber composition according to claim 1, wherein the amount of the adhesive agent in the adhesive silicone rubber composition is from 0.01 to 50 parts by weight per 100 parts by weight of the organopolysiloxane containing an alkenyl group.

6. The adhesive silicone rubber composition according to claim 1, wherein the amount of the adhesive agent in the adhesive silicone rubber composition is from 0.1 to 5 parts weight per 100 parts by weight of the organopolysiloxane containing an alkenyl group.

7. The adhesive silicone rubber composition according to claim 1, wherein the organopolysiloxane containing an alkenyl group is represented by the formula $R_aSiO_{(4-a)/2}$ wherein R is an substituted or unsubstituted monovalent hydrocarbon group, letter a is a number from 1.9 to 2.4, and the content of alkenyl group is from 0.01 to 10 mol % of the entire R groups.

8. The adhesive silicone rubber composition according to claim 7, wherein the content of alkenyl group is from 0.1 to 1 mol % of the entire R groups.

9. The adhesive silicone rubber composition according to claim 1, wherein the organopolysiloxane containing an alkenyl group is selected from the group consisting of

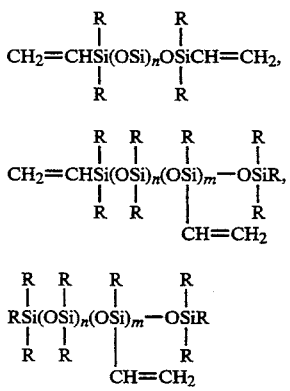

-continued and

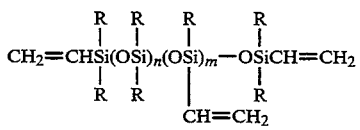

wherein R is a substituted or unsubstituted monovalent hydrocarbon group, excluding an aliphatic unsaturated group, and letters m and n are positive numbers and m+n=100 to 5000 and m/(m+n)=0.001 to 0.1.

10. The adhesive silicone rubber composition according to claim 1, wherein the amount of the organohydrogenpolysiloxane in the adhesive silicone rubber composition is from 0.4 to 5 equivalents per alkenyl group in the organopolysiloxane containing an alkenyl group.

11. The adhesive silicone rubber composition according to claim 1, wherein the amount of the organohydrogenpolysiloxane in the adhesive silicone rubber composition is from 0.8 to 2 equivalents per alkenyl group in the organopolysiloxane containing an alkenyl group.

12. The adhesive silicone rubber composition according to claim 1, wherein the addition reaction catalyst is platinum, a platinum compound, rhodium, or a rhodium compound.

13. The adhesive silicone rubber composition according to claim 12, wherein the amount of the addition reaction catalyst in the adhesive silicone rubber composition is from 0.1 to 1000 ppm of platinum or rhodium based on the total composition.

14. The adhesive silicone rubber composition according to claim 12, wherein the amount of the addition reaction catalyst in the adhesive silicone rubber composition is from 1 to 200 ppm of platinum or rhodium based on the total composition.

15. The adhesive silicone rubber composition according to claim 1, wherein the adhesive agent is

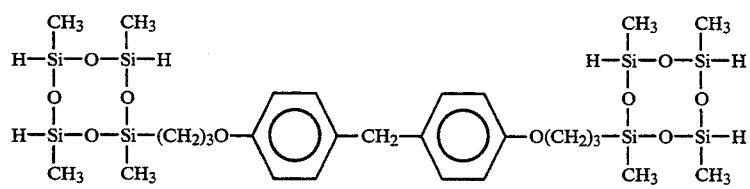

or

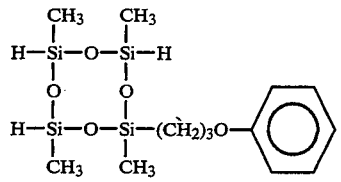
-continued
16. The adhesive silicone rubber composition according to claim 1, wherein the adhesive agent is
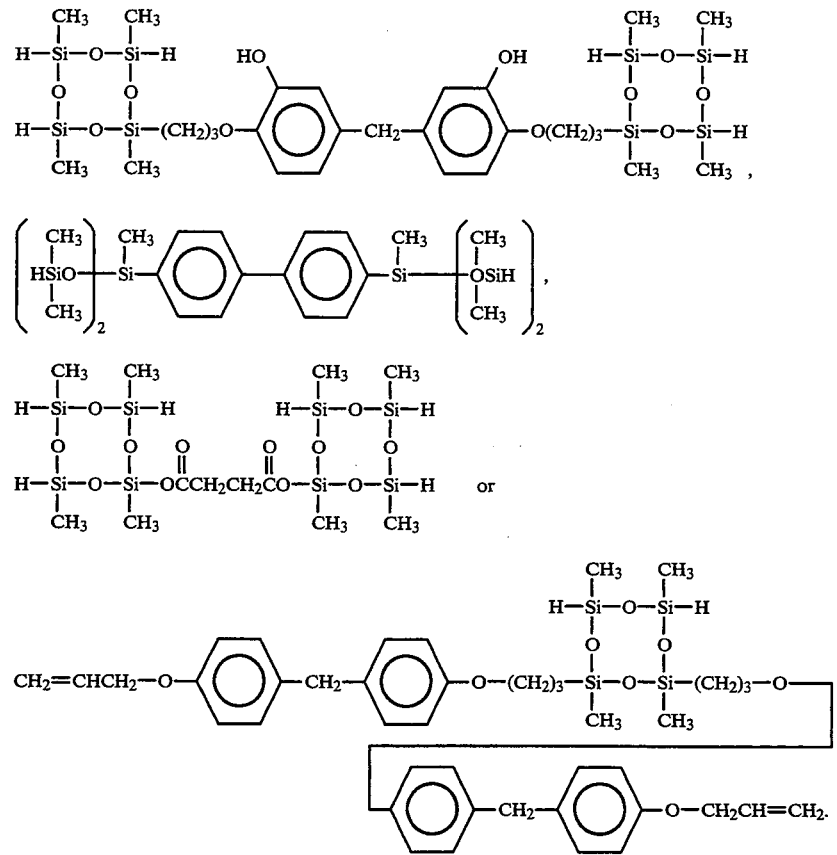
* * * * *